(12) United States Patent
Frenk et al.

(10) Patent No.: US 8,460,349 B2
(45) Date of Patent: *Jun. 11, 2013

(54) BONE SCREW

(75) Inventors: Andre Frenk, Brittnau (CH); Florian Beutter, Solothurn (CH); Franco Cicoira, Selzach (CH)

(73) Assignee: Synthes USA, LLC, West Chester, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/591,838

(22) Filed: Aug. 22, 2012

(65) Prior Publication Data

US 2012/0316607 A1     Dec. 13, 2012

Related U.S. Application Data

(63) Continuation of application No. 10/861,818, filed on Jun. 4, 2004, now Pat. No. 8,273,113, which is a continuation of application No. PCT/CH01/00698, filed on Dec. 4, 2001.

(51) Int. Cl.
    *A61B 17/86* (2006.01)
(52) U.S. Cl.
    USPC ............ 606/315; 606/316; 606/275; 411/412
(58) Field of Classification Search
    USPC .................. 606/315–317, 275; 411/412, 413, 411/415
    See application file for complete search history.

(56) References Cited

U.S. PATENT DOCUMENTS

| | | | | |
|---|---|---|---|---|
| 5,019,079 A | * | 5/1991 | Ross | 606/312 |
| 5,375,956 A | * | 12/1994 | Pennig | 411/389 |
| 8,216,243 B2 | * | 7/2012 | Yevmenenko et al. | 606/99 |
| 8,273,113 B2 | * | 9/2012 | Frenk et al. | 606/315 |
| 2005/0033300 A1 | * | 2/2005 | Frenk et al. | 606/72 |

* cited by examiner

*Primary Examiner* — Eduardo C Robert
*Assistant Examiner* — Julianna N Harvey
(74) *Attorney, Agent, or Firm* — Fay, Kaplun & Marcin, LLP

(57) ABSTRACT

A device for manipulating bone fragments includes a bone screw includes a shaft extending along a longitudinal axis. The shaft includes a first end having a first threaded portion with a first core diameter, a first external diameter and a first pitch. The shaft includes a second end having a second threaded portion with a second core diameter, a second external diameter and a second pitch. The second end further has a tool engaging surface, wherein the first external diameter is no greater than the second core diameter, the first and second pitches are substantially equal, and a non-threaded middle segment between the first and second threaded portions, an outer diameter of the middle segment being smaller than the first core diameter, and wherein the shaft includes a cannulation extending therethrough disposed coaxial with the screw longitudinal axis. An installation instrument includes first and second ends, a longitudinal axis, and a bore extending along at least a portion of the longitudinal axis, the bore in communication with the first end of the instrument, wherein the bore has threads along at least a portion of a length thereof, the threads configured to mate with the second threaded portion of the bone screw so that rotating the installation instrument rotates the bone screw to drive the screw into a bone.

16 Claims, 2 Drawing Sheets

BONE SCREW

CROSS REFERENCE TO RELATED APPLICATION

The present application is a Continuation application of U.S. patent application Ser. No. 10/861,818 filed on Jun. 4, 2004 entitled "Bone Screw," now U.S. Pat. No. 8,273,123 which is Continuation of PCT Patent Application Serial No. PCT/CH2001/000698 filed on Dec. 4, 2001.

FIELD OF THE INVENTION

The invention relates to a bone screw for connecting two bone fragments, to a device for implanting such a bone screw, and to a method for setting, compressing and/or fixing bone fragments.

BACKGROUND OF THE INVENTION

Bone screws are used in various ways in osteosynthesis, for example, for setting bone fragments, as compression screws or for fixing bone fragments.

A bone screw with two axially terminal threaded segments and a middle threadless segment is known from U.S. Pat. No. 5,019,079 to Ross. The diameter of the middle segment corresponds essentially to the external diameter of the external thread at the distal threaded segment, but is larger than the core diameter of the external thread at the proximal threaded segment, so that the middle segment can be used for laterally stabilizing the two bone fragments of the fracture. It is a disadvantage of this construction of bone screws that the two external threads have different pitches, so that the different steps for the implantation, the setting the bone fragments, the compression of the bone fragments and the recessing of the screw head cannot be carried out separately from one another.

The invention is to provide a remedy to this problem. It is an object of the invention to create a bone screw, which enables the bone fragments to be set and compressed and the screw head to be recessed separately during the implantation.

SUMMARY OF THE INVENTION

Pursuant to the invention, this objective is accomplished with a bone screw, and with a device for implanting such a bone screw, as well as with a method for setting, compressing and/or fixing bone fragments.

The inventive bone screw comprises essentially two threaded segments, which are disposed coaxially with the longitudinal axis and terminally at the bone screw, the pitches $S_V$ and $S_H$ of the front and rear segments respectively being identical. After these two bone fragments have been set and compressed, wherein only the front threaded segment is screwed into the distal bone fragment while the rear threaded segment is screwed, for example, into an implantation instrument and not yet into the proximal bone fragment, the bone screw can be screwed further into the bone fragments, until the rear threaded segment also is recessed completely in the proximal bone fragment. This can be accomplished without at the same time changing the position of the bone fragments relative to one another and without changing the compression of the two bone fragments. The two threaded segments are constructed so that the external diameter of the front threaded segment is smaller than the core diameter of the external thread at the rear threaded segment.

The advantages of the inventive bone screw and the inventive device are that due to the pitch of the external thread at the front threaded segment and at the rear threaded segment being the same, the steps of setting the bone fragments, compressing the bone fragments, and recessing the head of the screw can be carried out separately and in a controlled manner.

Because the rear threaded segment is configured with a core diameter, which is larger than the external diameter of the front threaded segment, interaction of the rear threaded segment with the thread already cut in the bone fragments for the front threaded segment can be avoided.

Preferably, the external threads at the front and rear threaded segments are self-cutting threads.

A preferred embodiment of the inventive bone screw includes, between the two threaded segments, a middle, threadless segment, which has an external diameter, which is smaller than or equal to the core diameter of the external thread at the front threaded segment. With that, the front threaded segment can be screwed completely into the distal bone fragment and the borehole in the proximal bone fragment does not have to be enlarged relative to the borehole in the distal bone fragment for setting and compressing the bone fragments. Compared to an embodiments of known bone screws, the front threaded segment of which directly adjoins the rear threaded segment in the axial direction and for which the borehole in the proximal bone fragment would have to be enlarged so that the front threaded segment can be screwed only into the distal bone fragment, a higher stability of the connection between the bone screw and the proximal bone fragment can furthermore be attained with the present device.

The inventive device serves for setting, compressing and fixing bone fragments by means of a bone screw and includes a surgical implantation instrument, which has a central borehole through which a screwdriver can be passed, extending coaxially through the implantation instrument. Furthermore, the central borehole is expanded from the front end of the implantation instrument up to a depth T, so that a shoulder is formed at the depth T. In the expanded part of the central borehole, there is an internal thread, which is complementary to the external thread of the rear threaded segment of the bone screw, so that the rear threaded segment of the bone screw can be screwed into the central borehole up to a depth T. The depth T is selected so that $T \geqq L$, where L is the length of the rear threaded segment of the bone screw. With that, it can be achieved that the rear, threaded segment of the bone screw can be screwed completely into the central borehole of the implantation instrument.

BRIEF DESCRIPTION OF THE DRAWINGS

The invention and further developments of the invention are explained in even greater detail in the following by means of the partially diagrammatic representations of several examples. In the drawings.

DETAILED DESCRIPTION OF THE INVENTION

Figure 1:
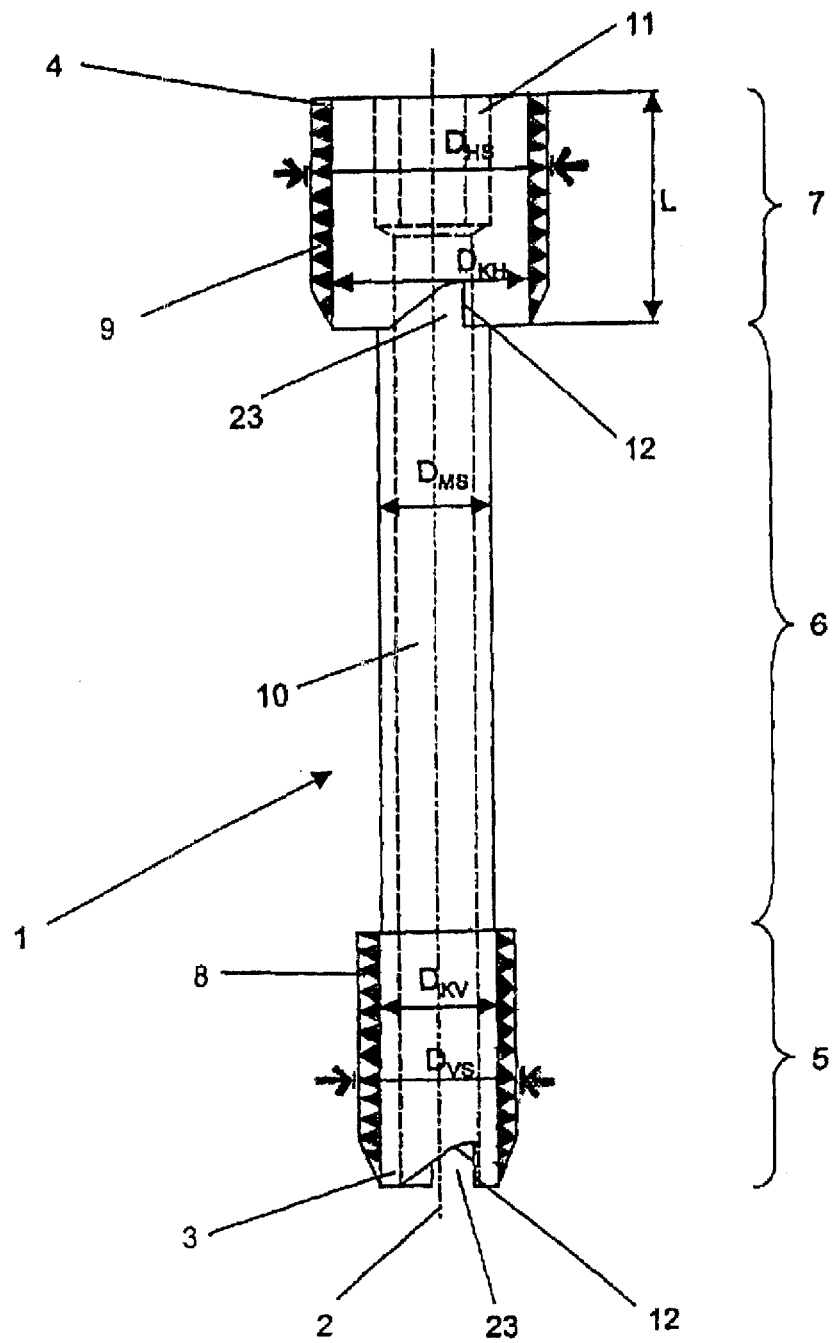
FIG. 1 shows a cross-sectional view of an embodiment of the inventive bone screw.

A preferred embodiment of the inventive bone screw 1 is shown in FIG. 1. This bone screw 1 includes a rear threaded segment 7 with an external thread 9, which has a core diameter $D_{KH}$, an external diameter $D_{HS}$ and a pitch $S_H$, a middle, threadless segment 6 with an external diameter $D_{MS}$, which adjoins the rear threaded segment 7 coaxially with the longitudinal axis 2, and a front threaded segment 5 with an external thread 8, which has a core diameter $D_{KV}$, an external diameter $D_{VS}$ and a pitch $S_V$. The two threaded segments 5, 7 have different diameters, that is, the core diameter $D_{KH}$ of the rear threaded segment 7 is larger than or equal to the external diameter $D_{VS}$ of the front threaded segment 5. However, the pitches of the two external threads 8, 9 are identical. The external diameter $D_{MS}$ of the middle segment 6 is smaller than or equal to the core diameter $D_{KV}$ of the front threaded segment 5. Moreover, at the front end 3 of the bone screw 1 and at the transition between the rear threaded segment 7 and the middle segment 6, several indentations 23, distributed over the periphery of the two threaded segments 5, 7 and aligned axially, are disposed with cutting edges 12 essentially parallel to the longitudinal axis 2, so that these two external threads 8, 9 are constructed as self-cutting threads. At the rear end of 4 of the bone screw 1, means 11 for accommodating a screwdriver, for example, a hexagonal recess, Torx or Phillips, are disposed coaxially. Moreover, the bone screw 1 is equipped with a central borehole 10, which extends from the front end 3 up to the rear end 4 and serves, for example, for accommodating a guiding wire (not shown).

Figure 2:
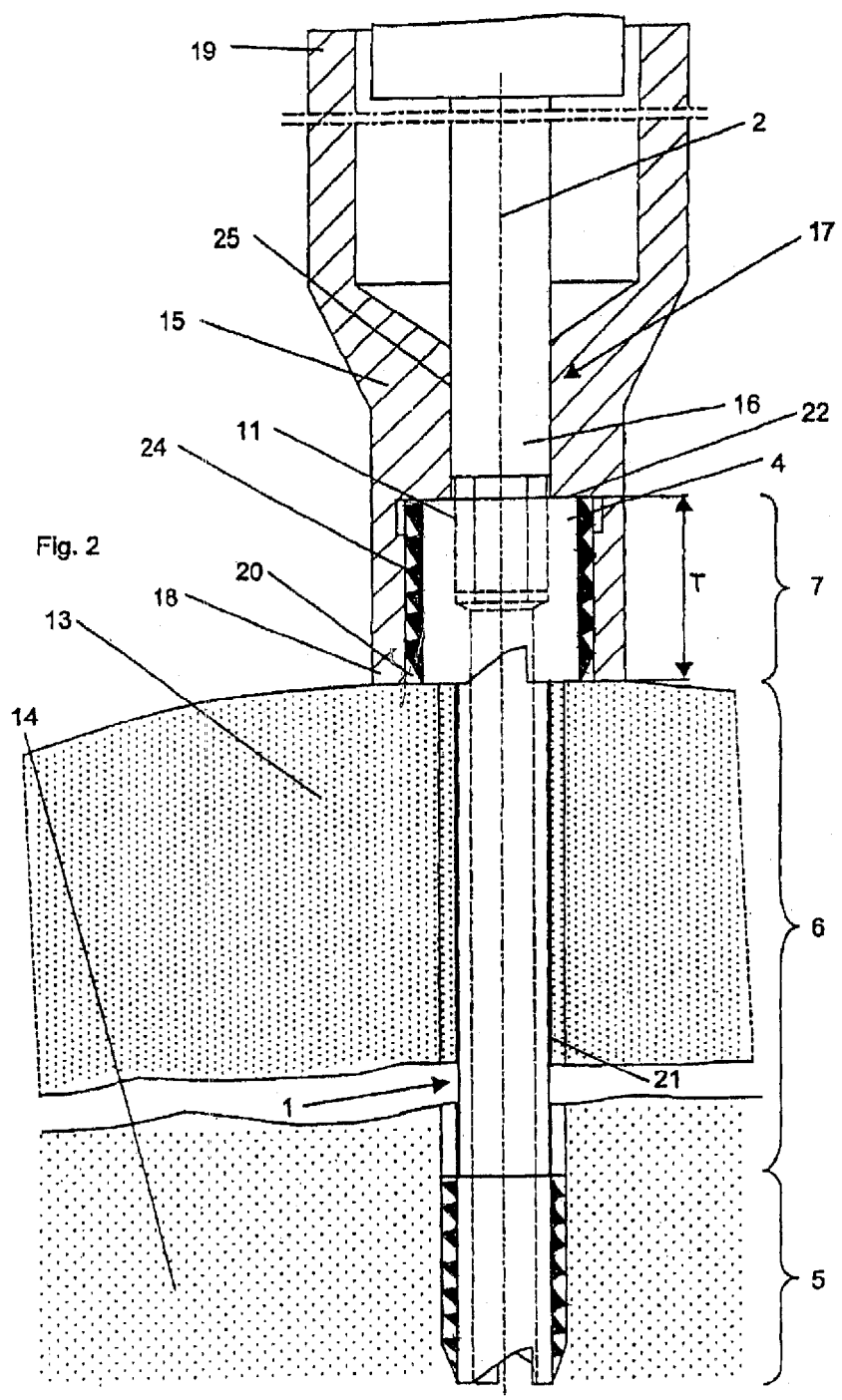
FIG. 2 shows a cross-sectional view of the embodiment shown in FIG. 1, an implantation instrument, and a screwdriver.

In FIG. 2, the inventive device is shown together with a bone screw 1, the rear threaded segment 7 is screwed completely into the implantation instrument 15 and the front threaded segment 5 of which is screwed completely into the distal bone fragment 14. The implantation instrument 15 includes a continuous central borehole 17, which is expanded from the front end 18 up to a depth T and, in expanded part 24, has an internal thread 20, which is complementary to the external thread 9. At the depth T, between the expanded part 24 of the central borehole 17 and the narrower part 25 of the central borehole 17, there is a shoulder 22, against which the rear end 4 of the bone screw 1 rests when the rear threaded segment 7 is screwed completely into the implantation instrument 15. A screwdriver 16 can be passed through the narrower part 25 of the central borehole 17 from the rear end 19 of the implantation instrument 15, so that the screwdriver 16 can be introduced into the means 11, which are disposed at the rear end 4 of the bone screw 1 for accommodating a screwdriver and the bone screw 1 can be rotated by means of the screwdriver 16 relative to the implantation instrument 15.

For setting, compressing and fixing the two bone fragments 13, 14, a borehole 21, passing through the proximal bone fragments 13 and into the distal bone fragment 14, is produced. The diameter of the borehole 21 corresponds to the core diameter $D_{KV}$ (FIG. 1) of the external thread 8 at the front threaded segment 5 of the bone screw 1.

At the start of the implantation process, the rear, threaded segment 7 of the bone screw 1 is screwed completely and up to a depth T in the internal thread 20 into the central borehole of the implantation instrument 15. By rotating the implantation instrument 15 about the longitudinal axis 2, the bone screw is then screwed into the pre-drilled boreholes 21 in the two bone fragments 13, 14. Since the rear threaded segment 7 of the bone screw 1 is taken up completely in the implantation instrument 15, the external thread 9 of the rear threaded segment 7 cannot engage the proximal bone fragments 13, so that, as the implantation instrument 15 is rotated, only the front threaded segment 5 of the bone screw 1 can be screwed into the distal bone fragment 14. In this phase, the front end 18 of the implantation instrument 15 assumes the task of a screw head, so that, after the bone screw 1 has been brought into the two bone fragments 13, 14 far enough that the front end 18 of the implantation instrument 15 lies against the proximal bone fragment 14, the two bone fragments 13, 14 are moved towards one another by rotating the implantation instrument 15 further. As soon as the two bone fragments 13, 14 are in contact with one another, compression of the two bone fragments 13, 14 commences. As soon as the desired compression of the two bone fragments 13, 14 has been reached by rotating the implantation instrument 15 further, the screwdriver 16 is inserted through the central borehole 17 in the implantation instrument 15 into the means 11 for accommodating the screwdriver and the bone screw 1 is rotated further with the screwdriver 16, so that, while the implantation instrument 15 is held in place, the bone screw 1 is screwed out of the internal thread 20 at the front end 18 of the implantation instrument 15 and the rear threaded segment 7 is screwed into the proximal bone fragments 13, until this the rear threaded segment 7 is brought completely beneath the surface of the proximal bone fragment 13. Since the two bone fragments 13, 14 are not moved relative to one another during this last process, the compression is unchanged after the rear, threaded segment 7 is driven into the proximal bone fragment 13.

Preferably, the bone screw 1 is used where a screw head would interfere, for example, for fractures in the vicinity of a joint, for intraarticular fixation such as scaphoid fractures, for small fragments and for fixations in the vicinity of sinews, nerves and vessels.

While the invention has been shown and described herein with reference to particular embodiments, it is to be understood that the various additions, substitutions, or modifications of form, structure, arrangement, proportions, materials, and components and otherwise, used in the practice and which are particularly adapted to specific environments and operative requirements, may be made to the described embodiments without departing from the spirit and scope of the present invention. Accordingly, it should be understood that the embodiments disclosed herein are merely illustrative of the principles of the invention, and that various modifications may be made by those skilled in the art which will embody the principles of the invention and fall within the spirit and the scope thereof.

The invention claimed is:

1. A device for manipulating bone fragments, comprising:
a bone screw including a shaft extending along a longitudinal axis, the shaft including a first end having a first threaded portion with a first core diameter, a first external diameter and a first pitch, a second end having a second threaded portion with a second core diameter, a second external diameter and a second pitch, the second end further having a tool engaging surface, wherein the first external diameter is no greater than the second core diameter, the first and second pitches are substantially equal, and a non-threaded middle segment between the first and second threaded portions, an outer diameter of the middle segment being smaller than the first core diameter, and wherein the shaft includes a cannulation extending therethrough disposed coaxial with the screw longitudinal axis; and
an installation instrument including first and second ends, a longitudinal axis, and a bore extending along at least a portion of the longitudinal axis, the bore in communication with the first end of the instrument,
wherein the bore has threads along at least a portion of a length thereof, the threads configured to mate with the second threaded portion of the bone screw so that rotating the installation instrument rotates the bone screw to drive the screw into a bone.

2. The device of claim 1, wherein the installation instrument bore further includes an internal shoulder for axially engaging the second end of the screw to prevent longitudinal movement of the screw within the bore when the second threaded portion is fully engaged with the bore threads.

3. The device of claim 1, wherein the first threaded portion has self-cutting threads for cutting bone.

4. The device of claim 3, wherein the first threaded portion comprises at least one surface disposed substantially parallel to the screw longitudinal axis configured for cutting bone.

5. The device of claim 3, wherein the second threaded portion comprises at least one surface disposed substantially parallel to the screw longitudinal axis configured for cutting bone.

6. The device of claim 1, wherein the cannulation is configured to receive a guide wire for guiding the screw into the bone.

7. The device of claim 1, wherein the second end of the bone screw further has a tool-receiving surface configured to receive a driving end of a driving tool for imparting rotational motion to the bone screw.

8. The device of claim 7, wherein the tool-receiving surface comprises a recess configured to be engaged by a screwdriver.

9. The device of claim 8, wherein the recess includes a hexagonal recess, a Torx recess or Phillips recess.

10. The device of claim 7, wherein the bore of the installation instrument is in communication with both the first and second ends of the instrument, the bore configured to allow at least the driving end of the driving tool to be placed therethrough to engage the tool-receiving recess of the bone screw when the screw is fully engaged with the bore threads.

11. A method for manipulating first and second bone fragments of a patient, comprising:
creating a hole in the first and second bone segments;
inserting a first end of a shaft of a bone screw having a first threaded portion with a first core diameter, a first external diameter, and a first pitch into the hole in the first bone segment, wherein the shaft includes a cannulation extending therethrough disposed coaxial with the screw longitudinal axis;
inserting a second end of the shaft of the bone screw into a bore of an installation instrument, the second end of the shaft having a second threaded portion with a second core diameter, a second external diameter, and a second pitch, the bore extending along at least a portion of a longitudinal axis of the installation instrument, the installation instrument comprising first and second ends, and the second end of the shaft engaging threads of the bore along at least a portion of a length thereof, the threads configured to mate with the second threaded portion of the bone screw, wherein the first external diameter is no greater than the second core diameter, wherein the first and second pitches are substantially equal, wherein a non-threaded middle segment is between the first and second threaded portions, an outer diameter of the middle segment being smaller than the first core diameter;
rotating the installation instrument to drive the first threaded portion of the screw through the first bone segment and into engagement with the second bone segment;
inserting a driving tool through the bore of the installation instrument to engage a tool engaging surface of the second end of the bone screw; and
rotating the tool to simultaneously drive the second threaded portion of the screw into engagement with the first bone segment and to unthread the second threaded portion from the bore of the installation instrument.

12. The method of claim 11, wherein the rotating of the installation instrument step includes compressing the first and second bone segments together.

13. The method of claim 12, wherein the inserting of the driving tool step causes no substantial additional compression of the first and second bone segments compared to that provided in rotating of the installation instrument.

14. The method of claim 13, further comprising:
driving the bone screw into the first bone segment so that the second end of the bone screw does not substantially protrude above a top surface of the first bone segment.

15. The method of claim 11, wherein at least the first threaded portion includes self-cutting threads configured to cut bone.

16. The method of claim 15, wherein the second threaded portion includes self-cutting threads configured to cut bone.

* * * * *